United States Patent [19]
Goodale

[11] Patent Number: 5,985,218
[45] Date of Patent: Nov. 16, 1999

[54] REAGENT CARTRIDGE

[75] Inventor: David L. Goodale, Yorba Linda, Calif.

[73] Assignee: Beckman Coulter, Inc., Fullerton, Calif.

[21] Appl. No.: 08/840,043

[22] Filed: Apr. 24, 1997

Related U.S. Application Data

[63] Continuation-in-part of application No. 08/675,586, Jul. 3, 1996, abandoned.

[51] Int. Cl.$^6$ ............................................. B01L 3/08
[52] U.S. Cl. ........................ 422/102; 206/569; 436/47
[58] Field of Search .................. 422/58, 64, 65, 422/102; 206/569; 436/47

[56] References Cited

U.S. PATENT DOCUMENTS

| | | | |
|---|---|---|---|
| 4,764,342 | 8/1988 | Kelln et al. ............................ | 422/72 |
| 4,849,177 | 7/1989 | Jordan ................................... | 422/64 |
| 4,933,147 | 6/1990 | Hollar et al. ........................... | 422/64 |
| 5,075,082 | 12/1991 | Fechtner ................................. | 422/102 |
| 5,149,501 | 9/1992 | Babson et al. ......................... | 422/58 |
| 5,167,922 | 12/1992 | Long ..................................... | 422/58 |
| 5,322,668 | 6/1994 | Tomasso ............................... | 422/104 |
| 5,538,691 | 7/1996 | Tosa et al. ............................. | 422/102 |

FOREIGN PATENT DOCUMENTS

| | | |
|---|---|---|
| 0 192 968 A2 | 9/1986 | European Pat. Off. . |
| 0 217 000 A2 | 4/1987 | European Pat. Off. . |
| 0 290 018 A2 | 11/1988 | European Pat. Off. . |
| 0 502 638 A2 | 9/1992 | European Pat. Off. . |
| 0 601 205 A1 | 6/1994 | European Pat. Off. . |

OTHER PUBLICATIONS

International Search Report.

*Primary Examiner*—Jill Warden
*Attorney, Agent, or Firm*—William H. May; Margaret A. Kivinski; Steven G. Roeder

[57] ABSTRACT

A one piece, injection molded single piece, well container suitable for reagents for use in a clinical instrument such as a protein analyzer, normally molded from a high density polyethylene or other recyclable plastic. The container is one or more wells, uses standard caps, and is readily adapted to automatic filling equipment. The molded, single piece reagent cartridge is used in a clinical instrument, the reagent cartridge comprised of a plurality of storage wells located in a line in fixed relationship. The reagent cartridge has a guide at one end which is engageable with a means on the receiving means on an analyzer to restrain the cartridge from radial or lateral movement. Each of the wells has side walls and a closed bottom, and the side walls have an upper terminal position including an access opening. An integrally formed hollow shell open at the bottom and otherwise substantially enclosing said wells from a point below the terminal portion is provided to form a hollow space within the shell around the exterior of the wells to permit the flow of conditioned air around the walls. Positive retention is provided by forming a hole through the wall, which engages a detent formed on the retention means.

18 Claims, 3 Drawing Sheets

5,985,218

REAGENT CARTRIDGE

This application is a continuation-in-part of U.S. application Ser. No. 08/675,586, filed Jul. 3, 1996, now abandoned.

BACKGROUND OF INVENTION

Various reagent cartridges for use in protein analyzers and other automated clinical analyzers are known.

Fechtner U.S. Pat. No. 5,075,082 describes a reagent cartridge for use in an automated clinical analyzer having a plurality of independent storage compartments and including a body member and a bottom wall. The body member and the bottom wall are separately formed by injection molding and then the individual parts are welded together using a metal plate heated to an elevated temperature which renders the adjoining surfaces of the body member and bottom wall fusible. In the Fechtner cartridge, the chambers for storing fluids are formed by the joinder of the bottom wall to the body member.

Boris et al U.S. Pat. No. 5,031,797 describes a reagent cartridge which has a plurality of chambers for containing fluid reagent, each chamber having an entry port and resealable seal means for receiving a probe used to withdraw reagent from the cartridge. A vent in the form of sealing or adhesive tape is provided for each chamber in the top closure. One end of the cartridge has a flange extending outwardly therefrom which includes a plurality of vertically aligned openings or windows through which an optical signal may be transmitted. The floor of the chambers have necks with access openings sealed with an elastomeric membrane which can be pierced by the probe to remove fluid reagent. The floor and the side and dividing walls of the cartridge are molded of a single piece. The top closure is fastened to the side and dividing walls by ultrasonic welding or by adhesive fastening. Ultrasonic welding is difficult to control and tends to yield significant numbers of units which are poorly bonded and prone to develop leaks. In addition, the use of ultrasonic welding tends to locally denature the resin from which the units are made. Consequently, both welded and adhesive bonded units are not homogenous in chemical composition over the entire unit.

The cartridge of the present invention is a one piece design using a low cost commodity resin which is recyclable, whereas the two piece designs of the prior art, which are either thermally welded, bonded together on a special heat metal plate fixture, or joined by adhesives, are "non-recyclable". The two piece design also places severe constraints on the types of resins which may be used since they must be inert to the reagents as well as "bondable" to each other. Because of this and the elimination of assembly tooling and procedures, the cartridge of the invention has a lower production cost.

The single piece cartridge of this invention has molded-in threads for one or more reagent chambers or wells which are adapted to receive screw-on caps including screw-on vented caps. The single piece cartridge may also contain "thinned out" areas strategically located to permit the observation of the fluid levels within the wells at any time. These and other advantages of the present invention will be apparent to those skilled in the art from the following more detailed description.

SUMMARY OF THE INVENTION

A single piece reagent cartridge for use in a clinical instrument having a reagent storage apparatus including a wheel for storing a reagent cartridge, the reagent cartridge comprising:

at least one storage well, said well including side walls and a closed bottom, said side walls having an upper terminal position including an access opening, and an alignment guide integrally formed with and extending from one end of the cartridge body, the free end of said guide being engageable with means on the wheel for restraining the cartridge from radial or lateral movement on the wheel.

The present invention further relates to a molded, single piece reagent cartridge for use in a clinical instrument which includes a storage apparatus having means adapted to support the reagent cartridge. The reagent cartridge comprises one or more of storage wells located in a line in fixed relationship. Each of the wells includes side walls and a closed bottom, and are generally cylindrical in shape. The side walls have an upper terminal portion including an access opening. An integrally formed hollow shell open at the bottom and otherwise substantially enclosing the wells from a point below the terminal portion provides a hollow space within the shell around the exterior of the wells. The hollow space provides for the circulation of conditioned air around the wells to maintain or control the temperature of the fluid contents. An open space is provided between the lower ends of the wells which is adapted to receive the means adapted to support.

In one embodiment, the invention provides an injection molded, single piece reagent cartridge for use in a clinical instrument which includes a storage apparatus having means adapted to support the reagent cartridge. The reagent cartridge comprises a plurality of storage wells located in a line in fixed relationship, each of the wells including side walls and a closed bottom, the side walls having a threaded terminal portion including an access opening and adapted to receive a threaded closure engageable with the threads on the terminal portion of the side walls to provide a fluid tight seal on each well. This embodiment also includes an integrally formed hollow shell open at the bottom to allow the circulation of conditioned air within the shell around the exterior of the wells and otherwise substantially enclosing the wells from a point below the threaded terminal portion to provide a hollow space within the shell around the exterior of the wells. An open space between the lower ends of the wells is adapted to receive the means adapted to support.

The invention further includes a reagent cartridge storage apparatus including a wheel or carousel for storing a reagent cartridge for use in a clinical instrument, wherein the wheel includes means adapted to support the reagent cartridge on the wheel. The reagent cartridge itself comprises a molded, single piece body that includes a plurality of storage wells located in a line in fixed relationship, each of the wells including side walls and a closed bottom; the side of walls having an upper terminal portion including an access opening. As noted above, the integrally formed hollow shell open at the bottom provides a hollow space within the shell around the exterior of the wells. An open space between the lower ends of the wells receives the means adapted to support and hold the reagent cartridge in a predetermined position on the wheel. This means may include a round or square hole in one or both sides of the cartridge shell which engages a feature included on the wheel to provide a "snap" fit.

A reagent cartridge storage apparatus including a wheel for storing a reagent cartridge for use in a clinical instrument, wherein the wheel includes means adapted to receive a guide formed on the cartridge, the reagent cartridge comprises a molded, single piece body including;

at least one storage well, said well including side walls and a closed bottom; said side walls having an upper terminal portion including an access opening, and a guide integrally formed with and extending from one end of the cartridge body, the free end of said guide being engageable with said means to receive to restrain the cartridge form radical or lateral movement on the cartridge.

In another important aspect, the invention includes an injection molded, single piece reagent cartridge for use in a clinical instrument which includes a storage apparatus having means adapted to support the reagent cartridge, the reagent cartridge being made of a translucent plastic and further including:

a integrally formed hollow shell open at the bottom to allow the circulation of conditioned air within the shell around the exterior of the wells and otherwise substantially enclosing wells from a point below the threaded terminal portion to provide a hollow space within the shell around the exterior of the wells, wherein the shell includes thinned out areas to provide see-through panels to permit observation of the fluid levels in the wells through the thinned out areas.

THE DRAWINGS

Turning to the drawings.

DESCRIPTION OF PREFERRED EMBODIMENTS

Figure 1:
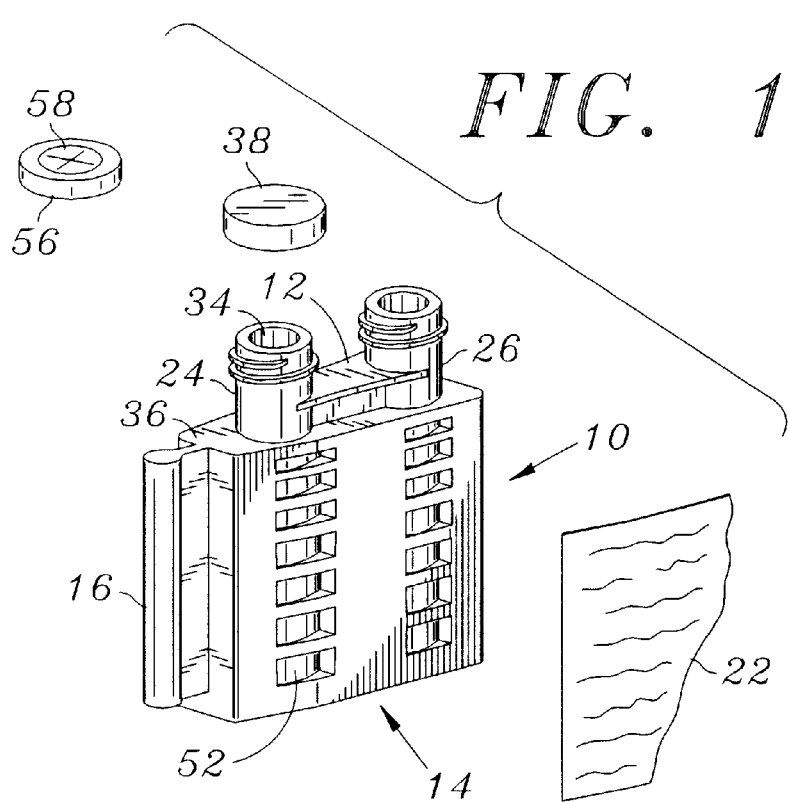
FIG. 1 is a perspective view of a preferred embodiment of this invention.

This invention provides a low cost, one piece, multi-well cartridge suitable for reagents used on the Analyzer System of concurrently filed U.S. patent application Ser. No. 08/946, 313. The cartridge is adapted to be inert to reagents normally employed in clinical analyzers, as it is preferably injection molded from high density polyethylene which is a recyclable material. The design is easily adapted to automatic filling equipment and utilizes inexpensive standard screw on caps. This cartridge allows filling with two component chemistries which are common for protein chemistries. In certain cases the two wells may be filled with the same reagent or buffer solutions as required for the particular assay.

In a preferred embodiment, the shape of the cartridge is unique and functional in that it fits on a reagent wheel in a space saving array of 24 cartridges. It is extremely easy to load on the wheel, but is retained in a positive manner. Since the shape is basically rectangular (except for a tapered "nose" to fit on the wheel more compactly), the cartridge is also adaptable to linear as well as rotary systems.

As shown in the drawings, the one piece cartridge 10 comprises a molded-in handle 12, a hollow shell 14, a molded in guide 16, a tapered "nose" 18, and multiple reinforcing ribs 20 to allow for placement of a label 22 on one or both exterior sides of the shell 14. The cartridge shown has a pair of integral spaced apart wells 24 and 26, each having a closed bottom 28, cylindrical side walls 30 and integrally molded external male threads 32 at the neck adjacent the upper access opening 34. The wells 24 and 26 are enclosed by the shell 14 from the point at which the flat top surface or flange 36 of shell 14 projects outwardly from and joins the exterior of the wells 24 and 26 below the threaded portion of the bottoms 28 of the wells. The hollow shell 14 enclosing the wells is skirt-like at its sides and open at the bottom. The sides of hollow shell 14 are generally spaced apart from the wells and the lower extremities of the sides of the hollow shell are generally approximately coterminous with the bottoms of the wells. A threaded linered cap 38 is threadably engageable with threads 32 on the neck of each of the wells 24 and 26.

Figure 4:
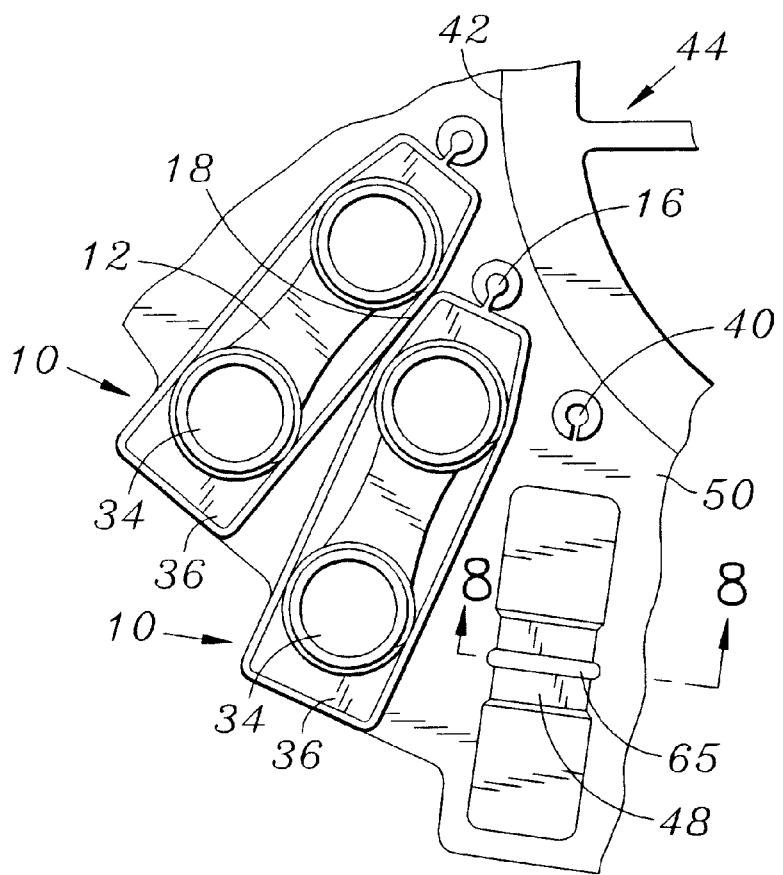
FIG. 4 is a top view showing the insertion of the embodiment of FIG. 1 into the reagent wheel of an analyzer system.
Figure 5:
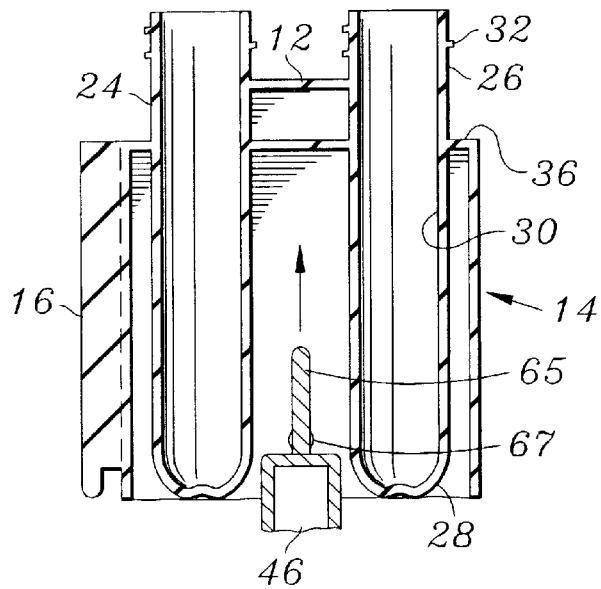
FIG. 5 is a sectional view of the embodiment of FIG. 3 taken along the line 5—5.
Figure 7:
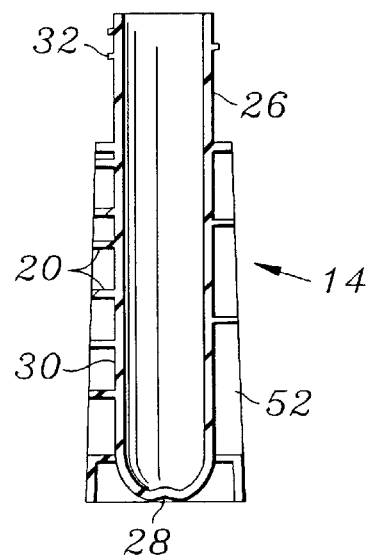
FIG. 7 is a sectional view taken along the line 7—7 in FIG. 6.

As shown in FIG. 4, the alignment guide 16, which is aligned with the center line of wells 24 and 26, is inserted into the corresponding slot 40 in a molded column 42 provided in the reagent carousel or wheel 44 of the rotary clinical analyzer system. The engagement of guide 16 with slot 40 is similar to a key in a key hole. The open space 46 between wells on the cartridge 10 fits over a saddle 48 molded into the reagent wheel rim 50. This prevents rotation of the cartridge 10 about the guide 16. As shown in FIGS. 4–8, a wedge shaped fin 65 can be molded into the center of each saddle 48 to provide a slight interference fit of the cartridge 10. On one side of the fin 65 a protrusion or detent 68 is molded. When positioned on the reagent wheel rim 50, the cartridge 10 snaps into place when a hole 67, formed through one side of the hollow shell 14 engages the detent 68. Insertion and removal force for the cartridge 10 is a function of entry for angle 69 and exit angle 70 on each side of the detent 68. The cartridge 10 with surrounding shell 14 being hollow on the bottom side (see FIG. 5), allows the external walls of the wells 24 and 26 within the shell 14 to be exposed to the ambient air and temperature conditions surrounding the cartridge 10. The reagent wheel 44 also has corresponding holes to allow conditioned air to circulate within the shell 14 around wells 24 and 26 for either cooling or heating purposes. The free circulation of controlled temperature air within the shell 14 (indicated by the arrows in FIG. 5) and around the exterior of the wells 24 and 26 is of benefit in maintaining the desired temperature conditions of the contents of the wells. Many of the reagents normally used in the wells are sensitive to temperature and to changes in temperature, and are subject to degradation if the temperature is not maintained within allowable limits.

Tapered nose 18 allows for close packing of the cartridges to reduce the diameter of the wheel to make it smaller and reduce inertia.

Figure 3:
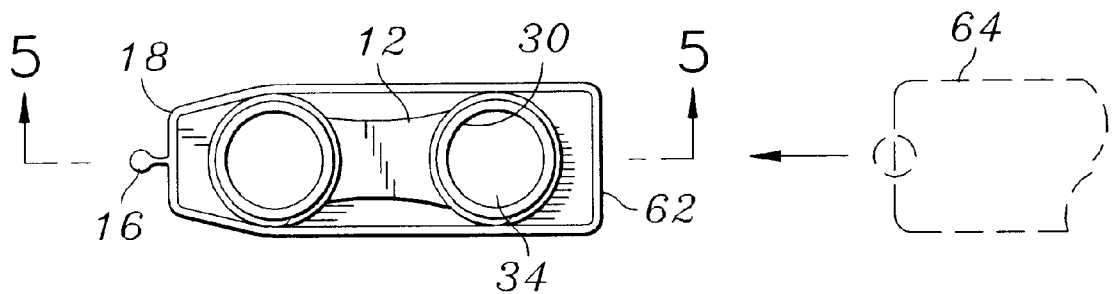
FIG. 3 is a top view of the embodiment of FIGS. 1 and 2.
Figure 6:
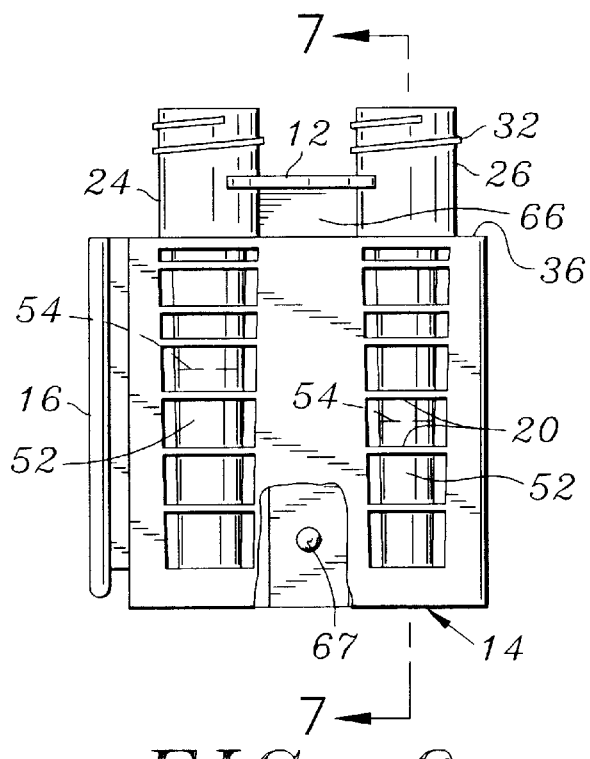
FIG. 6 is a side view of the embodiment of FIGS. 1 to 5.
Figure 8:
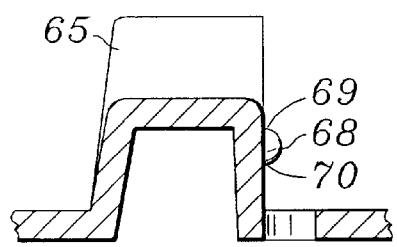
FIG. 8 is a sectional view of the saddle and tapered fin showing a detent feature to lock the cartridge onto the reagent wheel of the analyzer system. It is taken from FIG. 4 along 8—8.

FIGS. 3 and 6, top view and side view, respectively, show thinned out areas in the molded shell 14 to create inset see-through panels 52 between reinforcing ribs 20, so that the fluid level 54 can be seen through the shell 14 and the translucent plastic well wall 30. At the inset panels 52, the shell 14 and translucent well wall 30 are preferably fused to form a reduced overall thickness of plastic. In preparing the cartridge for insertion on reagent wheel 44, the screw caps 36 are removed and replaced with evaporation caps 56. The evaporation caps 56, preferably made of silicone rubber, are provided with two cross slits 58 and are adapted to fit on each well to reduce evaporation of costly reagents once the cartridge has been installed on the clinical analyzer. The cross slits 58 are self-closing. As noted above, the cartridge has been provided with a hole in one or both walls of the shell 14 between the wells 24 and 26 which engage a protrusion or protrusions on the means adapted to support the reagent cartridge. This method of retention prevents the probe on the reagent cartridge storage apparatus, which is raised and lowered through the slitted evaporation cap, from dislodging or lifting the cartridge from its position.

Figure 2:
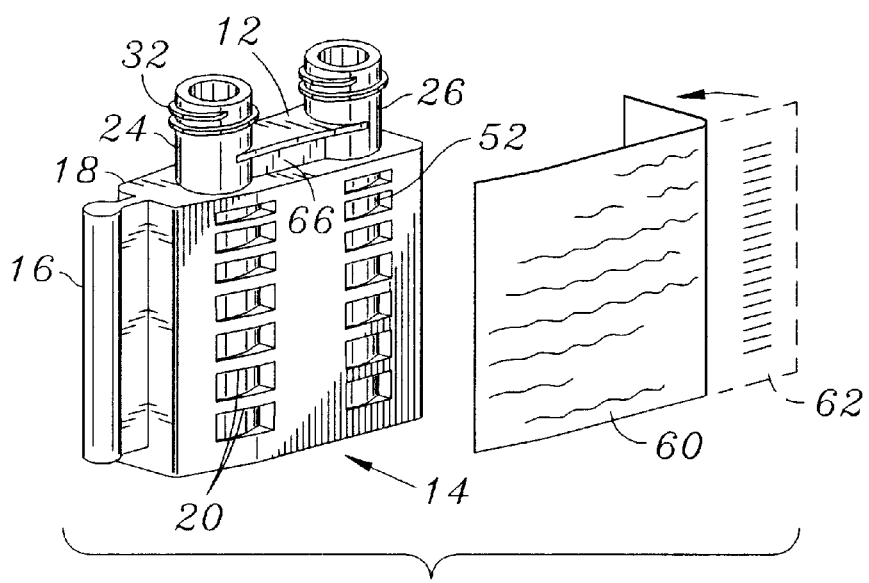
FIG. 2 is a perspective view of the embodiment of FIG. 1 with different labeling.

A different label 60 may be used (see FIG. 2), which can wrap around the exposed end of the cartridge, with a barcode 62 providing information, such as lot number, and reagent data, readable by a barcode reader 64 (FIG. 3).

The handle 12 in a preferred embodiment forms a bridge between the wells 24 and 26. The handle is generally parallel to the flat top surface 36. The handle 12 is integrally formed with vertical web 66 which extends between the underside of handle 12 and the top surface 36.

The concept of the reagent cartridge can be extended to any number of wells, and still be made as a single part. Although the wells used typically have a maximum capacity of approximately 10 ml, this volume can be increased by making the wells deeper or bigger in diameter. A larger diameter necessitates a larger cap, because the mouth of the wells must be at least as large as the diameter of the well. If it is desired to make the well to hold a much larger capacity of reagent, the well can be made in an oblong or oval shape, using a snap-on lid of the same shape. In addition, since the shape of the cartridge 10 is essentially rectangular, the cartridge will work well in a "linear" handling system, as well as rotational.

The basic advantages of the cartridge system of this invention are: a) low cost; b) single part (no assembly required); c) the use of commodity resins (used in high volumes and inexpensive); d) unique fit of the cartridge on the system (key in slot); e) injection molding provides high output with low cycle time, further reducing cost; f) use of recyclable plastic resin (environmentally "friendly"); g) ribs facilitate labelling; h) reduced evaporation (provided with an evaporation cap); and i) positive retention on wheel by means of the snap fit between detent on the wheel and a hole in the cartridge a wall.

The cartridge walls are preferably made of thin, flexible, resin. Such flexibility allows repeated insertions and removals of the cartridge onto the reagent wheel, without undue wear on the reagent wheel detent or having to maintain precision tolerances on the detent feature.

Having described the invention, it is intended that it be limited only by the lawful scope of the appended claims.

We claim:

1. A reagent cartridge for use with a clinical instrument, the clinical instrument including a wheel which moves the reagent cartridge, the wheel including means for restraining the cartridge, the reagent cartridge comprising:

a cartridge body which is formed as a single piece structure, the cartridge body comprising: (i) a pair of spaced apart storage wells, each storage well having side walls, a closed bottom, and an upper access opening; and (ii) an integrally formed hollow shell open at the bottom and otherwise substantially encircles the storage wells from below the access opening to provide a hollow space within the shell around the exterior of said wells.

2. The reagent cartridge of claim 1 herein the cartridge body is tapered at one end and includes an open space between the lower ends of said wells which receives said means to support and hold the cartridge in a predetermined position.

3. The reagent cartridge of claim 1 wherein the reagent cartridge at one end of the body includes an alignment guide and said wheel includes a slot which receives said alignment guide.

4. The reagent cartridge of claim 1 where there are two storage wells and an integrally molded handle forms a bridge between the wells.

5. The reagent cartridge of claim 1 wherein the sides of the hollow shell includes areas which receive labeling and barcode information.

6. A reagent cartridge for use with a clinical instrument, the clinical instrument including means for restraining the cartridge, the reagent cartridge comprising:

a cartridge body which is formed as a single integral unit, the cartridge body comprising: (i) a pair of storage wells, each storage well having side walls, a closed bottom, and an upper access opening; and (ii) a hollow shell which substantially encircles the wells, the shell providing space around the storage wells for circulating a conditioned fluid within the shell around the storage wells.

7. The reagent cartridge of claim 6 wherein the cartridge body includes an alignment guide which engages the means for restraining the cartridge to secure the cartridge body to the clinical instrument.

8. The reagent cartridge of claim 7 wherein the cartridge body includes an open space proximate a lower end of each of the wells, the open space being sized and shaped to receive a fin on the clinical instrument to hold the cartridge body in a predetermined position on the clinical instrument.

9. The reagent cartridge of claim 8 wherein the cartridge body includes a hole which is sized and shaped to engage a protrusion on the fin of the clinical instrument.

10. The reagent cartridge of claim 7 wherein the cartridge body is tapered proximate the alignment guide, wherein the cartridge body includes a handle which forms a bridge between the wells below the access opening, and wherein the shell includes areas which receive labeling and barcode information.

11. The reagent cartridge of claim 6 wherein the cartridge body is molded and made of a translucent high density polyethylene.

12. The reagent cartridge of claim 6 wherein each storage well includes a threaded portion proximate to the access opening, each threaded portion is sized and shaped to receive a threaded cap to enclose each access opening.

13. The reagent cartridge of claim 6 wherein the shell includes an open bottom end.

14. A reagent cartridge for use with a clinical instrument, the clinical instrument including a wheel which moves the reagent cartridge, the wheel including means for restraining the cartridge, the reagent cartridge comprising:

a cartridge body comprising: (i) a pair of storage wells, each storage well having side walls, a closed bottom, and an upper access opening; (ii) an alignment guide which engage the means for restraining to secure the cartridge body to the wheel; and (iii) a hollow shell which substantially encircles the storage well from a point below the access opening, the shell providing space around the storage well for circulating a conditioned fluid within the shell around the storage well.

15. The reagent cartridge of claim 14 wherein the shell includes an open bottom end.

16. The reagent cartridge of claim 14 wherein the shell includes a thinned out area to permit observation of the fluid levels in the wells.

17. The reagent cartridge of claim 14 wherein the cartridge body is molded and formed as a single integral unit.

18. A reagent cartridge for use with a clinical instrument, the clinical instrument including a wheel which moves the reagent cartridge, the wheel including means for restraining the cartridge, the reagent cartridge comprising:

a cartridge body which is formed as a molded, single piece, integral unit, the cartridge body comprising: (i) a pair of spaced apart storage wells, each storage well having side walls, a closed bottom, and an upper access opening; and (ii) an integrally formed hollow shell open at the bottom and otherwise substantially encircles the storage wells from below the access opening to provide a hollow space within the shell around the exterior of said wells, the shell providing space around the storage wells for circulating a conditioned fluid within the shell around the storage wells.

* * * * *